United States Patent [19]

Casida, Jr.

[11] Patent Number: 5,232,850
[45] Date of Patent: Aug. 3, 1993

[54] PREDATORY PSEUDOMONAS STRAIN AS A CONTROL OF BACTERIAL AND FUNGAL PLANT PATHOGENS

[75] Inventor: Lester E. Casida, Jr., State College, Pa.

[73] Assignee: The Penn State Research Foundation, University Park, Pa.

[21] Appl. No.: 732,563

[22] Filed: Jul. 19, 1991

[51] Int. Cl.$^5$ .............................................. C12N 1/20
[52] U.S. Cl. ................................. 435/253.3; 435/874; 435/875; 435/876; 435/877
[58] Field of Search ..................... 435/253.3, 874, 875, 435/876, 877

[56] References Cited

U.S. PATENT DOCUMENTS

| | | | |
|---|---|---|---|
| 3,625,940 | 12/1971 | Suzuki et al. | 435/886 |
| 3,992,528 | 11/1976 | Graham et al. | 435/898 |
| 4,569,841 | 2/1986 | Liu | 435/252.1 |
| 4,642,131 | 2/1987 | Hoitink | 435/253.3 |
| 4,827,079 | 5/1989 | Evans et al. | 435/240.51 |
| 4,996,049 | 2/1991 | Haefele et al. | 435/253.3 |

*Primary Examiner*—Nathan M. Nutter
*Attorney, Agent, or Firm*—Thomas J. Monahan

[57] ABSTRACT

A biologically pure culture of naturally-occurring Pseudomonas strain 679-2 is described. This nonobligate bacterial predator microorganism and its extracellular products are useful for the control of many bacterial and fungal diseases of plants. Whole cells of this bacterium and the antimicrobial compounds that it produces are involved in biological control effects. Materials and methods of preparation and application involving Pseudomonas strain 679-2 and its antimicrobial products are described.

2 Claims, No Drawings

PREDATORY PSEUDOMONAS STRAIN AS A CONTROL OF BACTERIAL AND FUNGAL PLANT PATHOGENS

GOVERNMENT SUPPORT

This invention was made with Government support under Contract DAAG29-85-K-0084 awarded by the Department of the Army. The Government has certain rights in this invention.

BACKGROUND OF THE INVENTION

The invention herein described relates to a microorganism and the use of this non-obligate bacterial predator of bacteria for the control of bacterial and fungal plant diseases. In particular, it is concerned with the use of a newly-isolated, highly-competitive, gram negative bacterial predator species for such control. Both the cells of this bacterium and the antimicrobial compounds that it produces are involved in the described biological control system.

By way of background, the use of living microbial cells to fight plant disease has received considerable attention in recent years [Lukezic, F. L., et al., in *New Directions in Biological Control: Alternatives for Suppressing Agricultural Pests and Diseases*, Alan R. Liss, Inc., New York (1990)]. However, the use of non-obligate bacterial predators of bacteria or fungi [Casida, L. E., Jr., Microb. Ecol. 15:1-8 (1988)] has not previously been considered in this context. The non-obligate bacterial predators live in soil. They use soluble nutrients in the environment, but if these are not available, they feed by attacking various other bacteria or fungi in the vicinity. Some of these predators can attack other bacterial predators, which means that interlocking food chains are created. Some, but not all, of these predators have distinct requirements for small amounts of certain metals. They use these metals to aid in breaking dormancy so they can initiate growth. The metals are not needed, however, for the ensuing growth. When these metals are poorly available in the environment, the predators elaborate specific peptide compounds that scavenge and sequester the metals so they will be available. Magnesium and copper are examples of these metals. The grams negative bacterial predators that need copper are resistant to copper and produce a peptide copper growth initiation factor (Cu-GIF) to obtain it. An example is *Cupriavidus necator* [Makkar, N. S., et al., Int. J. Syst. Bacteriol. 37:323-326 (1987)]. Bacteria like this seem to be at the top of the predatory hierarchy. Their predatory activity is helped by the fact that the Cu-GIF compound itself is quite toxic to other organisms. Therefore, when the predator cell attaches to a prey cell it can deliver a lethal dose of sequestered copper to aid in killing the prey cell.

An object of this invention is to isolate and develop a biologically pure, naturally-occurring microorganism capable of being used for the biological control of fungal and bacterial plant diseases.

It is also an object of this invention to develop materials and methods for the growth of said biological control microorganism and application to plants afflicted with bacterial and fungal diseases.

It is a further object of the invention to develop methods for the control of bacterial and fungal plant diseases using a naturally-occurring microorganism. These and other objects and advantages of the invention will become readily apparent from the following description and are particularly delineated in the appended claims.

SUMMARY OF THE INVENTION

In accordance with the present invention, a biologically pure Pseudomonas sp. (designated strain 679-2; strain ATCC 55089) is described. This naturally-occurring microorganism is a non-obligate bacterial predator useful for the control of a wide variety of bacterial and fungal plant diseases, including but not limited to Early Blight disease of tomatoes (*Alternaria solani*), Common Leaf Spot of alfalfa (*Pseudopeziza medicaginis*), and Spring Leaf Spot of alfalfa (Phoma). Strain 679-2 produces an inhibitor compound and a peptide copper growth initiation factor (Cu-GIF) particularly useful for the control of plant pathogenic bacteria and fungi. Various bacteria and fungi are shown to be inhibited by the inhibitor compound. Either whole cell compositions or filtrate are toxic to such pathogens. Materials and methods of preparation and applications of the biological control system of the invention are described.

DETAILED DESCRIPTION OF THE INVENTION

It has now been found that there is another, new, naturally-occurring, representative of the copper-resistant, nonobligate bacterial predators that can destroy even as powerful a predator as *C. necator*. This is because the new predator, which has been designated as strain 679-2, strain ATCC 55089, produces a toxic, antimicrobial, non-peptide, inhibitor compound in addition to the Cu-GIF. The inhibitor compound inhibits many, but not all, bacteria and fungi. Thus, a method using the cells and products of strain 679-2 to control fungal and bacterial diseases of plants has been developed. This method includes ways of preparing the cells for use so they will be able to live for either a short or a prolonged time after their introduction into nature.

A wide variety of bacteria and fungi has been shown to be inhibited by strain 679-2. In addition to its use as a biological control of fungal and bacterial plant diseases, strain 679-2 is a useful organism for bioremediation or sewage treatment. It exhibits strong selective competitive characteristics supportive of such applications.

Bacterial predator strain 679-2 appears to be a new species of Pseudomonas. This conclusion is based on its morphological and physiological characteristics. It is a gram negative rod, about $0.5-0.6 \times 0.8-0.9$ μm. It is motile by a single subterminal flagellum. It is oxidase negative. It grows well aerobically, but also can grow to a limited extent anaerobically without nitrate being added. It accumulates poly-$\beta$-hydroxybutyric acid (PHB) in its cells. It does not produce either fluorescent or non-fluorescent pigments. It is resistant to 0.01% $CuCl_2.2H_2O$. Its occurrence is rare in nature. To date, it has been found only in the soil at one site. It has not been found in other soils or on the leaves of various plants, although, if introduced, it can survive well in these habitats.

Once present in soil, strain 679-2 survives for prolonged periods. For example, $8.0 \times 10^7$ cells per g soil decreased to $2.0 \times 10^7$, $9.0 \times 10^6$, and $3.8 \times 10^5$, respectively, after 1, 2, and 3 months presence in the soil. In addition, counts of $5.8 \times 10^4$ and $6.0 \times 10^3$ cells per g soil were obtained in March for bacteria applied more than 6 months previously.

Strain 679-2 growing on an agar medium usually has a well-defined colony appearance resembling a beehive.

A culture with this colony appearance is called the "wild type." A few of the wild type colonies may change in appearance after several successive transfers of the wild type are made on agar. These altered colonies are relatively flat and are designated as "variant" colonies. The variant colonies are genetically relatively stable when they are subcultured. They are less able to protect plants against disease than are the wild type cells.

Pseudomonas strain 679-2 is deposited with the American Type Culture Collection, Rockville, Ma., and is accessioned as ATCC 55089.

The following examples are given solely for the purpose of illustration and are not to be construed as limitations of this invention, many variations of which are possible without departing from the spirit or scope thereof.

EXAMPLE 1

Control of Mixed Microbial Populations

Although found occurring naturally in only one soil to date, strain 679-2 is highly competitive when it is added to other soils. For example, 3 cells added to 1 g of soil increased in number to $4 \times 10^4$ cells within 24 hours. This is 0.1% of the total microflora of the soil and represents a generation time in nature of 105 minutes. When 0.8 mg L-glutamic acid was added along with the cells (to increase production of the inhibitor compound and the Cu-GIF), the respective values were $1 \times 10^6$ cells, 0.9%, and 75 minutes. Addition of a slightly greater number of cells to 1 g of soil, $8.0 \times 10^3$, resulted in strain 679-2 becoming 22% of the total population (162 minutes generation time) or, with 0.8 mg glutamic acid also added, 33% of the total population (105 minutes generation time). For all of these examples, the total count per se of soil organisms did not increase. For trials such as the above, the inhibitor compound could be added in place of L-glutamic acid since the latter was used by the organism to make the inhibitor.

EXAMPLE 2

Protection of Tomatoes Against Early Blight Disease

The following method was employed for growing cells of strain 679-2 for application to plants. Strain 679-2 was grown 20 hours at 28° C. on six slants of 0.1 strength heart infusion 1.5% agar medium. The cells were then suspended by loop by adding 4 ml sterile distilled water to each slant. The resulting cell suspensions were combined in a sterile empty flask. One ml of this was used to inoculate each growth flask. Each 500 ml Erlenmeyer growth flask contained 100 of L-glutamic acid synthetic broth medium. This medium was composed of L-glutamic acid, 0.1%; $NH_4NO_3$, 0.1%; $KH_2PO_4$, 0.1%; $Na_2SO_4$, 0.02%; and NaCl, 0.02%; pH 7.2 with KOH. These flasks were incubated by shaking 2 days on a reciprocal shaker at 28° C. At the end of this time, the cells had just reached the maximum stationary growth phase, and autolysis had not yet started. This broth culture was used, as is, for application by spraying to plants. The cell numbers in the broth culture were $1.1 \times 10^7$ per mil. An assay of a cell-free filtrate made from this culture showed no inhibition or other activity against the test organisms, *Micrococcus luteus* and *Aspergillus niger*.

Tomato plants already growing in the field were used. Early Blight disease (*Alternaria solani*) was endemic in these fields. Duplicate trials were conducted in separate fields. Three well-separated plants in each field were sprayed, and three non-sprayed plants in each field were used as controls. The culture was sprayed on the plants as a mist so the leaves just became damp. About $3.7 \times 10^9$ cells in total were sprayed toward each plant, but a part of these cells went onto the ground. Each plant received 3 of these sprayings, with spacings of 4 and 3 days between the sprayings. The plants and soil were evaluated 7 days after the last spraying. The incidence of *Alternaria solani* infection was based on the overall percent of leaf surface area that became infected. For plot number one, the means incidence values and standard deviations were, respectively, for treated and control plots, 7.9%, ±7.7 and 37.0%, ±23.7. For plot number 2, the respective values were 8.8%, ±7.4 and 28.7%, ±21.8. Based on the paired t-Test, the difference between treated and control plants was highly significant (1% probability level). The soil under the control plants did not contain any strain 679-2 cells, either initially or later on. At the time of the incidence of infection evaluations, the soil under the treated plants contained $3.2 \times 10^5$ 679-2 cells per g of soil. A test of this soil 44 days later (i.e., well after normal tomato harvest time) showed $1.6 \times 10^5$ 679-2 cells per g soil. The following spring (in March) $6.0 \times 10^3$ cells were still present. For these determinations, the soil was diluted and plated on 0.1 strength heart infusion 1.5% agar (pH 6.5) containing 0.01% $CuCl_2.2H_2O$. In contrast to these soil results, at the time of the evaluation of the incidence of *Alternaria solani* infection, there were no living cells of strain 679-2 on the tomato leaves. The leaves were macerated in a Waring blender and plated on copper agar. The lack of prolonged survival of 679-2 cells on the tomato leaves seemed to be due to a lack of desiccation protection. Each of the plants in the trial was well separated from other plants so there was no leaf canopy to help retain moisture. In a separate trial using plants that were sprayed only once with 679-2 cells and that were growing quite close together and receiving daily watering through the leaves, the 679-2 cells survived well. Initially after the spraying, the 679-2 cells were present at $5.4 \times 10^4$ per g of leaf tissue. This approximate number was found at sequential samplings. After 54 days, there were present $9.2 \times 10^3$ cells per g leaf. In this and all other trials, there was no sign of any leaf or plant toxicity or alteration caused by the presence of strain 679-2.

EXAMPLE 3

Alternate Procedure for Protection of Tomatoes Against Early Blight Disease

A field trial resembling that in Example 1 was conducted, but the strain 679-2 cells were grown initially in a different manner. They were grown such that they would survive less well in the field. Laboratory experiments had previously shown that strain 679-2 cells grown on full strength heart infusion agar were unaffected by incubation (storage) at either 4° or 28° C. for periods of from 9 to 25 days. Thereafter, they suddenly lost their copper resistance. A few days later (when the cells were about 13 to 39 days old), the cells died. The loss of copper resistance meant that the cells could no longer control their dormancy. In the field, the loss of copper resistance played an additional role, because the cells could no longer protect themselves from attack by other predator bacteria. Cells grown, as in Example 1, on a more dilute medium (e.g., 0.1 strength heart infusion broth or agar) did not demonstrate this programmed death.

Six full strength heart infusion agar slants were inoculated with strain 679-2 cells and incubated 48 hours at 28° C. The cells on each slant were then suspended by loop into 4 ml sterile distilled water. All cell suspensions were combined and centrifuged. The cell pellet then was washed once by centrifugation in sterile distilled water and, finally, resuspended in 100 ml of sterile distilled water. This suspension contained $1.0 \times 10^8$ strain 679-2 cells per ml. Each of 3 tomato plants with endemic Early Blight was sprayed with 33 ml of this cell suspension. This meant that a total of $3.3 \times 10^9$ cells was sprayed toward each plant, although some of the cells went onto the ground. The plants received only this one spraying. There was no plant toxicity evident during the trial, nor any other alteration in the plants attributable to strain 679-2. Fifteen days after application, the mean and standard deviation for percent disease incidence of treated leaves was, respectively, 27.7% and ±12.9. The corresponding values for the controls were 58% and ±2.8. The differences were highly significant (one percent probability level) based on the paired t-Test. Strain 679-2 cells were not found on the leaves at the time of the disease incidence evaluation, or on the fruits, or in the soil. Nevertheless, they had lived long enough to protect the leaves from *Alternaria solani*.

EXAMPLE 4

Protection of Alfalfa Against Common Leaf Spot

Strain 679-2 cells were prepared as in Example 2. An alfalfa field was used where Common Leaf Spot, *Pseudopeziza medicaginis*, was endemic. Twelve, well-separated, one-meter-square plots were marked off in the alfalfa field. Six of these were retained as untreated controls. The other six were sprayed with strain 679-2 broth culture. Each plot received 333 ml sprayed onto the leaves, although some ended up on the soil. Two additional, similar applications were made, with intervals between applications of 5 and 2 days, respectively. The evaluations of the percent incidence of disease and the survival of the 679-2 cells were made 12 days after the last spraying. For percent incidence of disease, the mean and standard deviation of the controls, respectively, were 5.5% and ±1.3. For treated plants, the values were 3.4% and ±1.0. The differences were highly significant (1% probability level) based on the paired t-Test. Strain 679-2 cells were not present initially in the soil, nor were they present on the leaves of the control plants or in their respective soils at the end of the experiment. At 12 days after the last spraying, the treated plants had $1.6\times10^5$ 679-2 cells per g of leaf tissue, and the soil beneath the plants contained $1.0\times10^6$ cells per g. Forty-five days after the last spraying, the soil still contained $4.2\times10^5$ 679-2 cells per g. The foliage had been cut (harvested) 25 days previous to this. Nevertheless, the foliage regrowth contained about $1.0\times10^3$ 679-2 cells per g of tissue. Approximately 6 months, which included overwintering, after the last spraying, the soil still contained $5.8\times10^4$ 679-2 cells per g soil. The cells were not present, however, on the alfalfa regrowth.

EXAMPLE 5

Protection of Alfalfa Against Spring Leaf Spot

Strain 679-2 wild type cells and variant cells were prepared individually as in Example 2. Petri plates of damp sterile sand were prepared. Three trifoliate leaflets of alfalfa were laid on the sand in each plate. Phoma fungus spores (that cause alfalfa Spring Leaf Spot disease) were sprayed onto the leaflets. Some of the plates that were sprayed with Phoma were also sprayed with the wild type cells of 679-2, and other plates with the variant cells. Additional Phoma plates received a mixture of the two types. All plates were then incubated one week at 22° C. The results showed that neither the variant nor the wild type cells were toxic to the leaves. The variant cells did not protect the leaves against Phoma. In fact, they interfered with the protection provided by the wild type cells when they were mixed with them. It was previously shown that the variant cells interfered with production of the inhibitor compound in broth cultures of strain 679-2 wild type cells. Protection of the leaves by the wild type cells was highly significant (1% probability level) based on the paired t-Test. The mean percent value and standard deviation for Phoma alone were 24.2% and ±13.7. When the wild type cells had been added with the Phoma spores, the values were 10.0% and ±7.5.

EXAMPLE 6

Lack of Plant Toxicity for Strain 679-2 Inhibitor Compound

The inhibitor compound and the Cu-GIF compound produced by strain 679-2 aid it in its attack on bacteria and fungi in nature. Strain 679-2 cells were grown 24 hours by shaking at 28° C. in 100 ml of full strength heart infusion broth. The cells were then separated from the broth and washed once by centrifugation in sterile distilled water. They were then resuspended in 100 ml of L-glutamic acid synthetic broth medium in a 500 ml Erlenmeyer flask as in Example 2. This flask was shaken 27 hours at 28° C. then frozen and thawed. The cells were removed by centrifugation, followed by passage of the supernate fluid through a 0.3 μm pore size membrane bacteriological filter. Assay against *M. luteus* showed that this filtrate contained 3.5 units per ml activity of the inhibitor compound. A second preparation was made by loop inoculation of strain 679-2 cells into 50 ml of full strength heart infusion broth in a 500 ml Erlenmeyer flask. This flask was shaken 64 hours at 28° C. It was then frozen and thawed, followed by centrifugation and filtration as above. The filtrate contained 41 units per ml activity of the inhibitor compound based on the *M. luteus* assay. Each of these preparations also contained a small amount of the Cu-GIF compound. Each preparation was sprayed so as to thoroughly wet the leaves of bean, tomato, and alfalfa plants in a greenhouse. There was no toxicity after 1, 4, or 6 days. In addition, the 3.5 unit per ml preparation was not toxic when it was applied as a leaf infusion into tobacco and tomato leaves. Infusion of the 41 unit per ml preparation for both plants produced necrotic lesions on the leaves. These did not occur if uninoculated sterile full strength heart infusion broth (the control) was infused.

EXAMPLE 7

Alternate Method for Producing Strain 679-2 Inhibitor Compound

The medium used was the L-glutamic acid synthetic broth described in Example 2. $MgCl_2.6H_2O$ at 0.05% was added, however, when the medium was prepared for the preservation flasks. The media were dispensed at 40 ml per 300 ml baffle-bottom Erlenmeyer flask for inoculum production, and at 50 ml per 500 ml Erlenmeyer flask for production of the inhibitor compound. The growth from a 20 hour full strength heart infusion agar slant of strain 679-2 was suspended in 5 ml of distilled water; 0.5 ml of this was then added to each inoculum flask. These were shaken on a reciprocal shaker 24 hours at 28° C. Five ml of this was used to inoculate each production flask. These were shaken 48 hours at 28° C., or until distinct autolysis had set in. The flasks were then frozen and thawed and the cells removed by centrifugation. The supernatant fluid was passed through an 0.3 μm pore size membrane filter. Preparations made in this manner usually assayed at about 2 to 9 units per ml, based on the *M. luteus* assay. In addition to the inhibitor compound, a small amount of Cu-GIF was present. If desired, the filtrate could be concentrated by use of a rotary vacuum evaporator operating at 60° C.

EXAMPLE 8

Inhibition of Microorganisms by strain 679-2 Inhibitor Compound

A variety of microorganisms was tested for sensitivity to the strain 679-2 inhibitor compound. Sensitivity testing involved the use of both cell-free concentrated preparations and perpendicular streaks on 0.1 strength heart infusion agar.

This medium contained 0.1% sucrose when Azotobacter or Saccharomyces were the test organisms. For the cell-free concentrated preparations, the test organism was streaked by loop in various directions to cover the surface of the agar in the plate. An absorbent paper disk (12.7 mm diameter of the type commonly used for assay of antibiotics) was then aseptically dipped in the preparation and placed on the agar surface in the center of the plate. After incubation for 1 to 3 days at 28° C., the diameter of the zone of inhibited growth of the test organism was measured. For the perpendicular streaks, strain 679-2 was grown 24 hours as a line of growth along one edge of the plate. Each test organism was then applied as a streak perpendicular to but not quite touching the strain 679-2 growth. Further incubation of 1 to 3 days showed whether the test organisms were being inhibited by any compounds being produced by strain 679-2 and diffusing into the surrounding agar medium. The distance of inhibited growth was measured.

Results of inhibition testing involving various bacteria and fungi are presented in Table 1. Note that *Agromyces ramosus, Actinomyces humiferus, Capriavidus necator* [N-1], *Ensifer adhaerens* [A and SA], and *Streptomyces* #34 are themselves bacterial predators of bacteria.

TABLE 1

Microbial Inhibition by strain 679-2 Inhibition Compounds

Very sensitive:
  *Micrococcus luteus*
  *Nocardia salmonicolor*
  *Arthrobacter globiformis* ATCC 8010
  *Azotobacter vinelandii* ATCC 12837
  *Azotobacter chroococcum* PSU 36
  *Agromyces ramosus* ATCC 25173
  *Agromyces ramosus* PSU 35
  *Actinomyces humiferus* ATCC 25174
  *Saccharomyces cerevisiae*
Sensitive:
  *Bacillus mycoides*
  *Escherichia coli*
  *Cupriavidus necator* PSU N-1, ATCC 43291
  *Ensifer adhaerens* PSU A, ATCC 33212
  *Ensifer adhaerens* PSU SA
  *Bacillus megaterium*
  *Streptomyces* PSU 34
  *Aspergillus niger*
  *Penicillium chrysogenum*
  *Rhizopus nigricans*
  *Mucor racemosus*
Borderline sensitivity (if any):**
  *Agrobacterium tumifaciens*
  *Bacillus thuringiensis* (Dipel)
  *Bacillus cereus*
  *Bacillus subtilis*
  *Rhizobium meliloti**
  *Mycobacterium phlei*   (large inhibition zones for concentrated preps have been seen at times)
No activity:
  *Streptococcus faecalis*
  *Pseudomonas aeruginosa*
  *Pseudomonas syringae* PSU 190
  *Geotrichum candidum*

*=Tested only with cell-free concentrated preparations. All other results were also obtained with perpendicular streaks on 0.1 HI agar with a 1 day head start for 679-2.
**=activity for perpendicular streak; concentrated prep.=inactive Thus, while we have illustrated and described the preferred embodiment of our invention, it is to be understood that this invention is capable of variation and modification, and we, therefore, do not wish or intend to be limited to the precise terms set forth, but desire and intend to avail ourselves of such changes and alterations which may be made for adapting the present invention to various usages and conditions. Accordingly, such changes and alterations are properly intended to be within the full range of equivalents and, therefore, within the purview of the following claims. The terms and expressions which have been employed in the foregoing specification are used therein as terms of description and not of limitation, and thus there is no intention in the use of such terms and expressions of excluding equivalents of features shown and described or portions thereof, it being recognized that the scope of the invention is defined and limited only by the claims which follow.

Thus is described out invention and the manner and process of making and using it in such full, clear, concise, and exact terms so as to enable any person skilled in the art to which it pertains, or to which it is most nearly connected, to make and use the same.

What is claimed is:

1. A biologically pure culture of Pseudomonas strain 679-2 (ATCC No. 55089).

2. A biologically pure microbial culture and mutants and variants thereof according to claim 1 capable of producing antimicrobial compounds.